(12) United States Patent
Aboul-Hosn et al.

(10) Patent No.: US 6,210,397 B1
(45) Date of Patent: Apr. 3, 2001

(54) SEALING CANNULA DEVICE

(75) Inventors: Walid Najib Aboul-Hosn; William Russell Kanz, both of Sacramento; Roland W. Ziegler, Cameron Park, all of CA (US)

(73) Assignee: A-Med Systems, Inc., West Sacramento, CA (US)

( * ) Notice: Subject to any disclaimer, the term of this patent is extended or adjusted under 35 U.S.C. 154(b) by 0 days.

(21) Appl. No.: 09/229,806

(22) Filed: Jan. 13, 1999

(51) Int. Cl.$^7$ ..................................................... A61M 25/16
(52) U.S. Cl. ........................ 604/533; 604/174; 604/164.11
(58) Field of Search .................................. 604/533, 174, 604/164, 264, 175, 166.01, 164.09, 164.1, 164.11, 164.04; 411/411

(56) References Cited

U.S. PATENT DOCUMENTS

| | | |
|---|---|---|
| 2,777,718 * | 1/1957 | Vegren . |
| 3,592,197 | 7/1971 | Cohen . |
| 3,717,151 | 2/1973 | Collett . |
| 3,856,021 | 12/1974 | McIntosh . |
| 4,069,826 | 1/1978 | Sessions et al. . |
| 4,338,937 | 7/1982 | Lerman . |
| 4,516,578 | 5/1985 | Shuffield . |
| 4,946,444 | 8/1990 | Heimke et al. . |
| 5,007,900 | 4/1991 | Picha et al. . |
| 5,064,417 | 11/1991 | Andreussi . |
| 5,098,398 | 3/1992 | Lundgren . |
| 5,103,804 | 4/1992 | Abele et al. . |
| 5,122,122 | 6/1992 | Allgood . |
| 5,167,634 * | 12/1992 | Corrigan, Jr. et al. ............... 604/160 |
| 5,176,697 | 1/1993 | Hasson et al. . |
| 5,217,441 * | 6/1993 | Shichman .............................. 604/283 |
| 5,230,862 | 7/1993 | Berry et al. . |
| 5,234,408 | 8/1993 | Griffith . |
| 5,234,455 | 8/1993 | Mulhollan . |
| 5,242,415 | 9/1993 | Kantrowitz et al. . |
| 5,358,488 | 10/1994 | Suriyapa . |
| 5,391,156 | 2/1995 | Hildwein et al. . |
| 5,452,733 | 9/1995 | Sterman et al. . |
| 5,456,714 | 10/1995 | Owen . |
| 5,549,565 | 8/1996 | Ryan et al. . |
| 5,591,191 | 1/1997 | Kieturakis . |
| 5,651,773 * | 7/1997 | Perry et al. ........................... 604/174 |
| 5,676,682 | 10/1997 | Yoon . |
| 5,741,234 | 4/1998 | Aboul-Hosn . |
| 5,755,697 | 5/1998 | Jones et al. . |
| 5,855,566 * | 1/1999 | Dunlap et al. ........................ 604/164 |

* cited by examiner

*Primary Examiner*—Sharon Kennedy
*Assistant Examiner*—Kevin C. Sirmons
(74) *Attorney, Agent, or Firm*—Jonathan Spangler

(57) ABSTRACT

This invention relates to a sealing cannula device which can be easily and properly inserted while effectively sealing an incision made during a surgical or non-surgical process. The sealing cannula device includes a cannula sleeve having an external flange and tissue engaging threads. The screw threads on the external surface of the cannula sleeve allows the device to be easily screwed through an incision made in a body cavity wall or blood vessel until the tissue abuts against the flange. The vessel or body cavity wall is compressed between the flange and a flat surface formed by the helical thread. An effective compression seal is formed between the device and cavity or vessel wall which protects the puncture site from environmental contaminants. An axial through hole in the device provides vascular or body cavity access during surgical or non-surgical procedures.

15 Claims, 11 Drawing Sheets

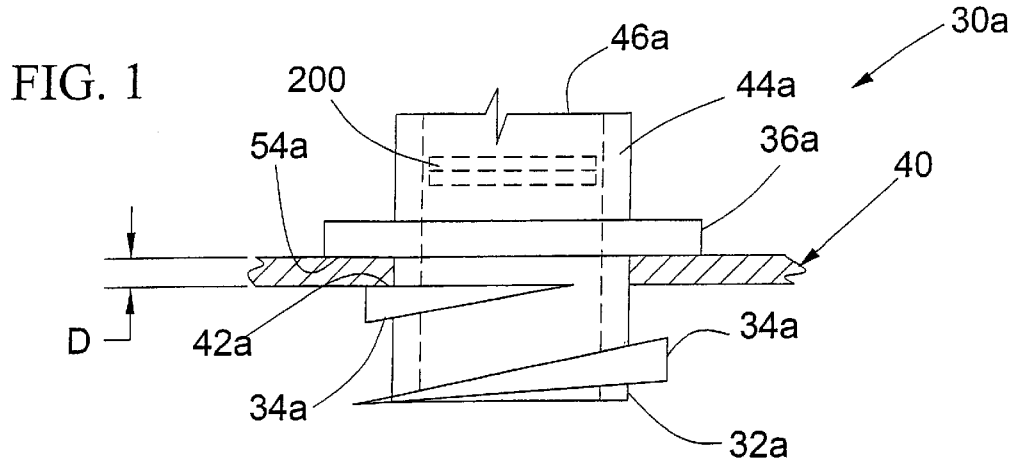
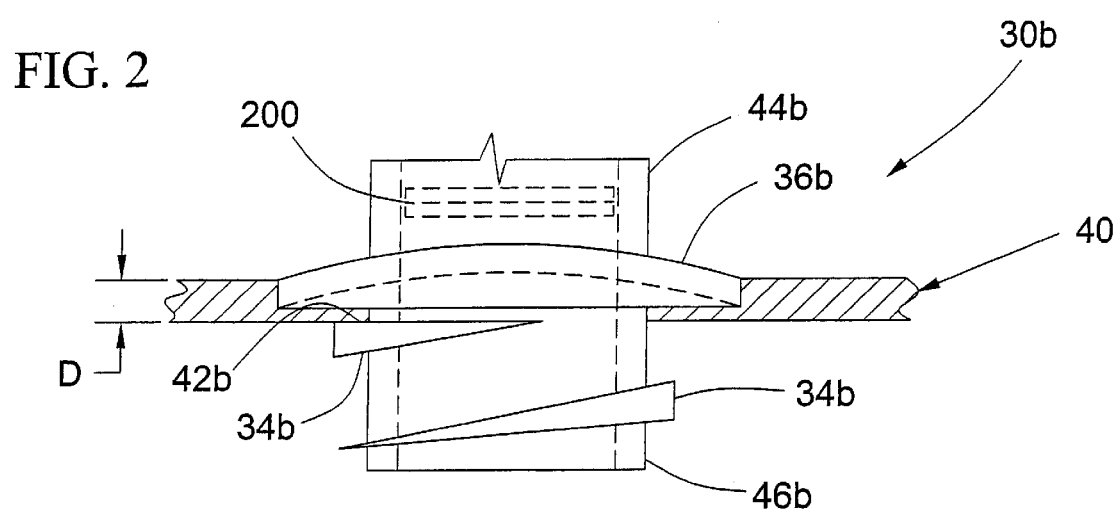
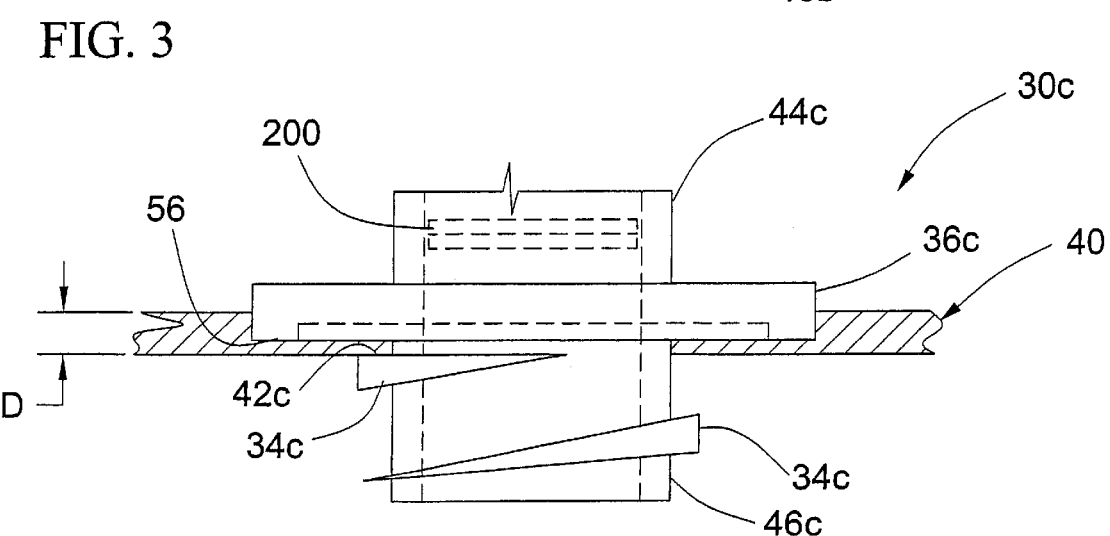

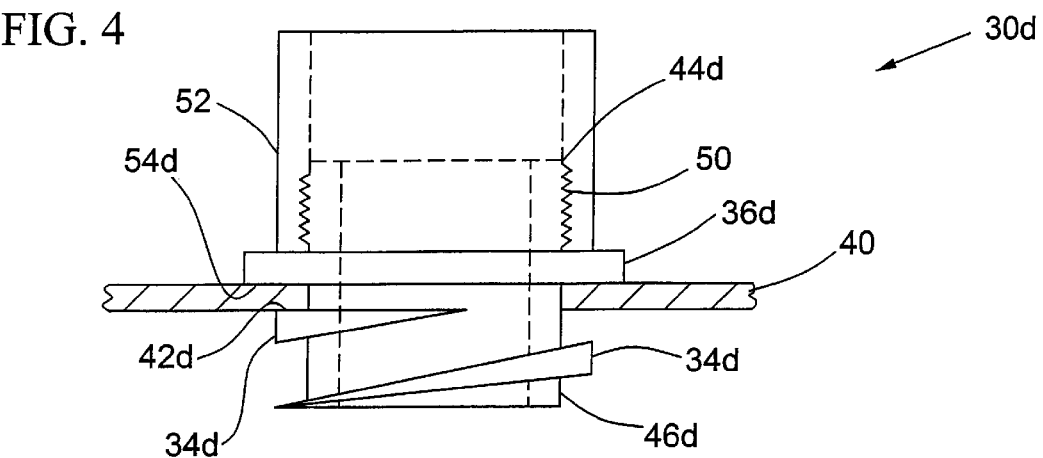
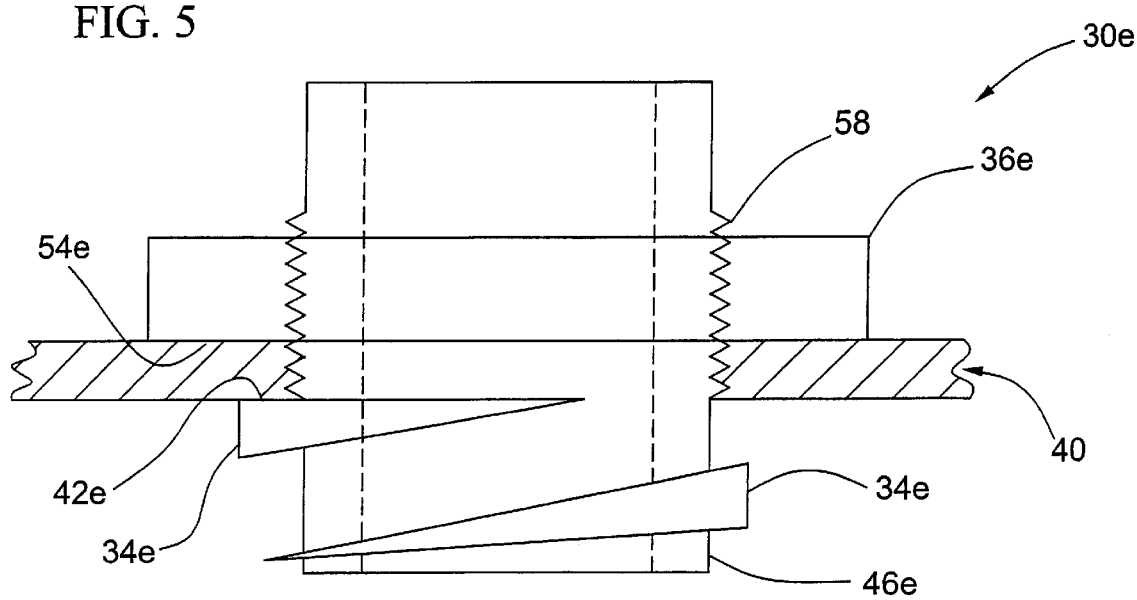

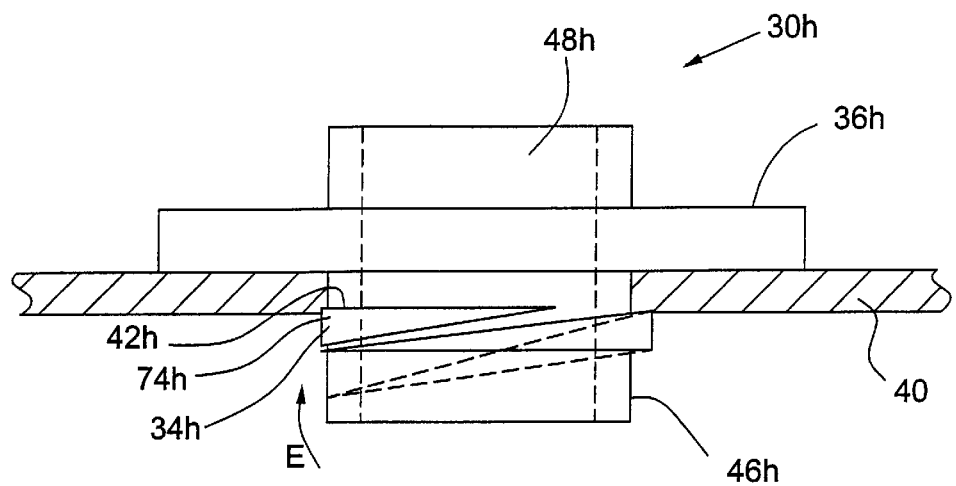
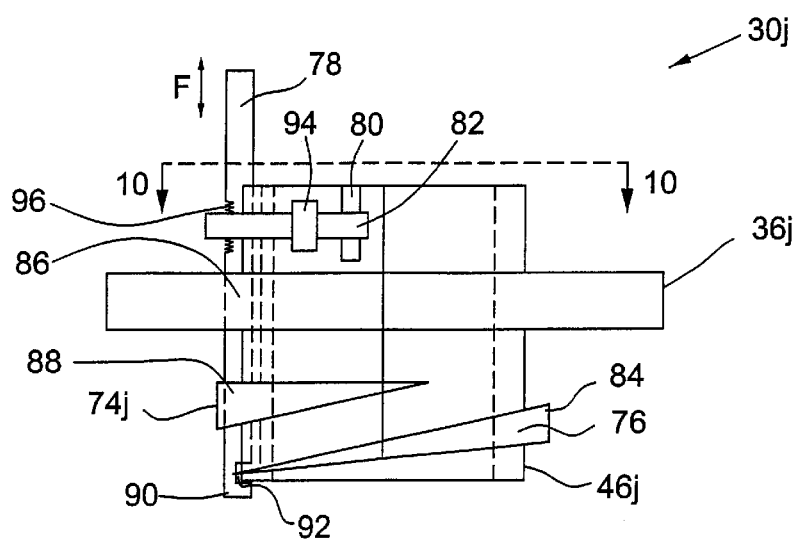

SEALING CANNULA DEVICE

BACKGROUND OF THE INVENTION

1. Field of the Invention

The invention relates to a surgical penetrating instrument, and more particularly, the invention relates to a cannula device that penetrates a body cavity or blood vessel and secures the device in a proper position while forming a seal between the device and body cavity or vessel wall.

2. Brief Description of the Related Art

The use of cannulas or trocars to obtain vascular and/or body cavity access is becoming more frequently practiced to achieve less invasive surgical procedures. A dilator can be used in combination with a cannula to enter vessels and arteries. Dilators are surgical instruments which have a sharp tip or stylet which is used to puncture tissue to form an opening through a patient's body tissue. In operation, a tube or cannula surrounds the dilator and both are inserted together into the patient's body. The dilator is then removed, leaving the cannula behind to act as a smooth conduit or pathway for subsequent insertion of surgical tools, such as catheters, graspers, or surgical viewing apparatus. For access to a body cavity, a trocar may be used to insert a cannula into the body cavity. Several cannulas may be employed during surgery in order to simultaneously receive several surgical instruments: an organ may be grasped and manipulated through one cannula, or pathway, while a surgical scalpel cuts away tissue using another trocar, and still another cannula is used to guide viewing endoscopes.

Utilizing such surgical equipment avoids the need to make a large surgical incision and use retractors to spread the sides of the incision to provide access for performing various surgical procedures. As described above, cannulas allow surgeons to access the interior of the body during non-open chest surgery; it is less invasive and less traumatic for the patient. Further, recovery from non-open chest surgery is typically shorter.

However, known cannula and trocar assemblies must be fitted with some sealing mechanism to prevent leakages of gasses or bodily fluids through the incision after inserting such assembly during the surgical procedure. Moreover, the cannula has a tendency to slide in and out of the incision, particularly when the surgeon is trying to manipulate surgical equipment through the cannula tube into or out of the body cavity. Further, infections may develop at an incision site directly exposed to contaminants in the environment for extended periods of time.

One example of a sealing mechanism is disclosed in U.S. Pat. No. 5,549,565 to Ryan, et al. This trocar and trocar tube assembly includes a removable disposable sealing valve portion and an optional sealing ring mounted in a groove located between an external flange and a threaded cannula sleeve. The sealing valve portion includes a sealing mechanism, such as an O-ring, seated inside the cannula base, a slit valve, a universal washer, and a covering cap. The valve assembly prevents leakages after the trocar is removed and the trocar tube is left inserted to provide portal access to the interior of the body. Although the Ryan sealing valve assembly prevents leakages of gases or bodily fluids through the surgical incision, this assembly requires several independent components to perform the sealing function, and each component constitutes a potential point of mechanical failure and/or leakage.

A second example of a sealing mechanism is disclosed in U.S. Pat. No. 5,755,697 to Jones, et al. This catheterization device has two main embodiments: screw-type and moly-type. The screw-type device includes a trocar and subcutaneous sleeve with coarse spiraling threads on its outer surface. When the trocar is rotated, the cutting blade is screwed into the skin until an annular skin cup, or retaining ring, abuts the skin surface. The annular cup is concave, thereby creating a seal against the patient's skin. The spiraling threads on the sleeve, coated with a tissue promoting substance, provide sealing and self-securing capabilities for the device. An opposite end of the device from the trocar's cutting end includes fine spiraling threads securing a cap or external lumen connection to the catheterization device. The moly-type device is similar to the screw-type device; however, the deformed moly-type device holds the catheterization device in the skin rather than the combination of threading and skin tension utilized by the screw device. Although the device described in Jones, et al. prevents leakages through the skin puncture where the device is positioned, this catheterization device requires the application of a tissue promoting substance, such as Dacron, to the spiral threading to effectively seal the puncture. This substance may be difficult to remove or harm the skin while removing the device. Such a coating substance may also result in allergic reactions. Further, the conical shape of the subcutaneous sleeve tapers toward the trocar and offers little support to that portion of the device external to the body from any movement or jostling that may occur during a surgical procedure.

SUMMARY OF THE INVENTION

The present invention relates to a sealing cannula device which can be easily and properly inserted to seal an incision and allow access to a body cavity, blood vessel, or the like during a surgical or non-surgical procedure.

Generally speaking, the present invention provides a cannula device that can be easily and properly inserted while effectively sealing the incision by using few components and without using tissue promoting substances, adhesives, or suture lines. In accordance with one aspect of the present invention, a sealing cannula device includes a cannula sleeve having an exterior flange and tissue engaging thread. The thread forms a surface which is substantially parallel to the bottom surface of the flange. The thread terminates a certain distance from the flange such that body tissue is trapped between the flange and thread.

In accordance with another aspect of the present invention, the sealing cannula device is incorporated into a surgical instrument. The sealing cannula device includes a cannula sleeve having an exterior thread that forms a surface which is substantially parallel to the bottom surface of the surgical instrument. The thread terminates a certain distance from the flange such that body tissue is trapped between the flange and thread. By incorporating the sealing cannula device into the surgical instrument, the need to utilize an outer cannula as an intermediary connector between the sealing cannula device and the surgical instrument is removed.

In accordance with an additional aspect of the present invention, the sealing cannula device includes a cannula sleeve having a flange and at least one pivoting member. The pivoting member is rotatably secured to the cannula sleeve. A slidable member or an inflatable balloon contacts the pivoting member such that the pivoting member rotates about a hinge and forms a surface which creates a seal with the body tissue. The body tissue is trapped between the pivoting member and a bottom surface of the flange. In a different configuration, the pivoting member is rotatably secured to the slidable member. When the slidable member moves with respect to the cannula sleeve, the pivoting member moves from a first position to a second position to trap body tissue between the members and a bottom surface of the flange.

In accordance with a further aspect of the present invention, the sealing cannula device includes a cannula sleeve having a flange, a plurality of flexible arms forming an opening, and a slidable member with an outer diameter larger than the opening. By moving the slidable member with respect to the cannula sleeve, the slidable member expands the flexible arms, thereby securing the device within the surgical opening.

In accordance with yet another aspect of the present invention, the sealing cannula device includes a cannula sleeve having a flange, a first portion with a first cross-sectional area, and a second portion with a second cross-sectional area. The second cross-sectional area is smaller than at least a portion of the first cross-sectional area and biases the body tissue against the flange. In a different configuration, the second portion is chosen to provide a compression fit between the bottom surface of the flange and the top surface of the first portion against the body cavity or vessel wall.

The present invention provides advantages of a single means for securing a cannula in the proper position while providing vascular or body cavity access during surgical or non-surgical procedures. Further, effective seals are formed between the device and cavity or vessel wall which protects the puncture site from environmental contaminants.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a partial side view of a first embodiment of a sealing cannula device with a flange;

FIG. 2 is a partial side view of another embodiment of the sealing cannula device with a concave flange;

FIG. 3 is a partial side view of another embodiment of the sealing cannula device with a lipped flange;

FIG. 4 is a partial side view of another embodiment of the sealing cannula device including a removable threaded external access port;

FIG. 5 is a partial side view of another embodiment of the sealing cannula device with an adjustable flange;

FIG. 8 is a partial side view of another embodiment of the sealing cannula device having a thread made from a temperature sensitive material so that one end of the thread flexes due to temperature changes;

FIG. 9 is a side view of another embodiment of the sealing cannula device having a pivoting thread with a trigger mechanism and a locking lever;

DETAILED DESCRIPTION OF THE PREFERRED EMBODIMENTS

Figure 6:
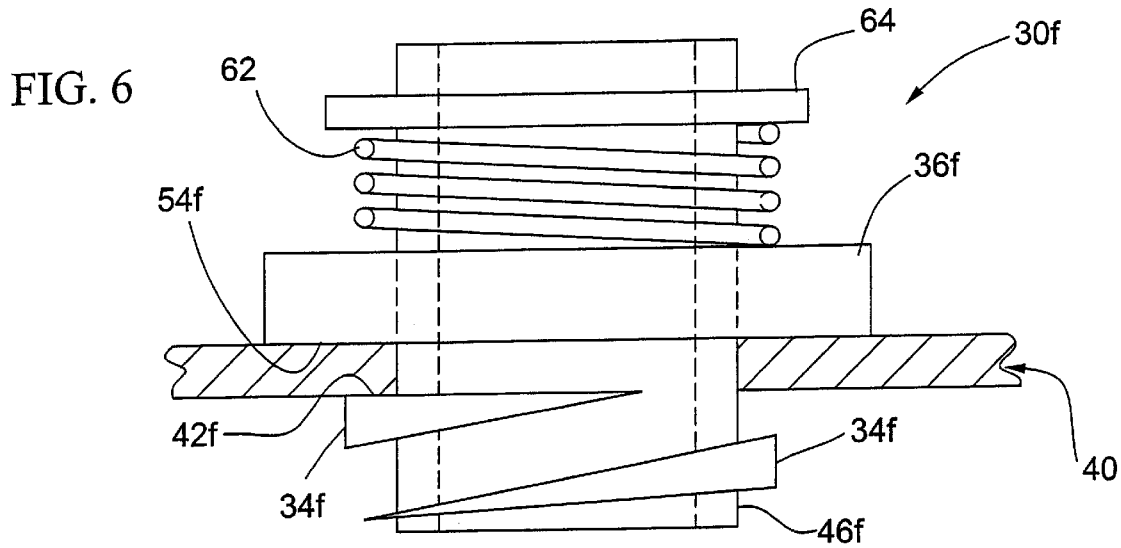
FIG. 6 is a partial side view of a further embodiment of the sealing cannula device with a spring biased adjustable flange.

As shown in FIG. 1, the sealing cannula device 30a in accordance with the present invention includes a hollow cannula sleeve 46a having a flange 36a for abutting an exterior surface of a blood vessel 40 through which the cannula has been inserted. The cannula sleeve 46a serves as a percutaneous conduit through which surgical tools or other medical devices obtain vascular or body cavity access during surgical procedures. According to one embodiment of the invention, the cannula sleeve 46a has an outer diameter of about 1 mm to about 40 mm, preferably about 3 mm to about 18 mm, and a wall thickness of about 0.008 mm to about 0.025 mm, preferably about 0.010 mm to about 0.016 mm. In the preferred embodiment, the cross-sectional configuration of the sealing cannula device 30a is circular; however, the sealing cannula device can have other cross-sectional configurations such as square, rectangular, or hexagonal. A proximal portion of the hollow cannula sleeve 46a provides an external access port 44a which may be used for securing the sealing cannula device 30a to an external medical device or outer cannula (not shown). The outer diameter of the external access port 44a may differ from the outer diameter of the distal portion of the cannula sleeve 46a.

In the first embodiment (shown in FIG. 1), the sealing cannula device 30a has a cannula sleeve 46a with a helical thread 34a on a lower portion 32a of the outer surface. A thread is defined as a projecting helical rib or spiral flange by which parts can be connected, and the external thread diameter, thread shape, and pitch may be either constant or varying along the longitudinal axis of the cannula sleeve. The angle between the lower surface 54a of the flange 36a and the upper surface 42a of the thread 34a is preferably in the range of about 0 degrees and 15 degrees, although those skilled in the art will appreciate that this range may vary without departing from the scope of the present invention. The thread 34a terminates a distance D from a lower surface 54a of the flange 36a. The distance D accommodates a thickness of the wall of a blood vessel, the skin, or other tissue 40. Preferably, the distance D is in the range of about 1 mm to about 5 mm, more preferably about 2 mm to about 3 mm. According to one embodiment, the flange 36a has a diameter of about 1.25 mm to about 50 mm, preferably about 3.5 mm to about 20 mm.

The thread 34a on the cannula sleeve 46a has an upper flat surface 42a which is substantially parallel to the bottom surface 54a of the flange 36a and substantially perpendicular to an axis of the cannula sleeve 46a. The distance D between the flat surface 42a of the thread 34a and the bottom surface 54a of the flange 36a is chosen to provide a compression fit between the flat surface and bottom surface against the skin, tissue, or vessel wall 40. The flange 36a may have various configurations, including but not limited to flat (shown in FIG. 1), concave (shown in FIG. 2), or lipped (shown in FIG. 3). The edges of the concave shaped flange 36b or lower surface 56 of the lipped flange 36c faces the flat surface 42b, 42c of the thread to create a tight seal between the sealing cannula device 30b, 30c and the vessel wall 40. Further, the sealing cannula device 30a can receive a hemostasis valve 200 inside the cannula, as shown in FIGS. 1–3, or can receive the hemostasis valve about the proximal end of the cannula sleeve 46a for sealing of the lumen. Examples of hemostasis valves are described in U.S. patent application Ser. No. 60/865,570, entitled "Hemostasis Valve with Membranes Having Offset Apertures", and Ser. No. 09/163,102, entitled "Self Sealing Hemostasis Valve", which are incorporated by reference in their entirety.

In another embodiment shown in FIG. 4, the external access port 44d has an outer surface with exterior threads 50 for attaching an outer cannula 52 or an external medical device, such as a blood pump. The outer cannula 52 attaches to the external access port 44d, and the thread 50 creates a fluid tight seal which prevents contaminants from violating this connection. This embodiment with the removable outer cannula or medical device allows the sealing cannula device 30d to be used with a variety of devices of various shapes and sizes.

In a fifth embodiment of FIG. 5, the flange 36e of the sealing cannula device 30e is adjustable along the longitudinal axis of the sealing cannula device 30e. The cannula sleeve 46e has an outer surface with a second helical thread 58 that terminates above or adjacent the thread 34e on the cannula sleeve. The flange 36e threadedly engages the exterior of the cannula sleeve 46e and is rotatable about its axial centerline. By rotating the flange 36e, the user may change the distance D between the lower surface 54e of the flange and the upper surface 42e of the thread 34e to tighten or loosen the seal between the flange and the vessel wall 40 and to accommodate different tissue thicknesses. In an alternative embodiment, the flange 36e threadedly engages the thread 34e. Accordingly, by rotating the flange 36e, the user may tighten or loosen the seal between the flange and the vessel wall 40 to accommodate different tissue thicknesses.

As illustrated in FIG. 6, a compressed spring 62 may be provided between the flange 36f and a second flange 64, fixed on the cannula sleeve and above the flange 36f. The flange 36f is movable along the longitudinal axis of the cannula device 30f. The compressed spring 62 biases the movable flange 36f towards the vessel wall 40, thereby securing the movable flange in place and helping create a tight seal between the flange 36f and the vessel wall 40. The adjustment means may alternatively comprise any other suitable means, including but not limited to ratchets or expandable materials. In another embodiment, the flange 36f has a threaded inner surface which engages a second thread on the exterior surface of the cannula sleeve 46f. In this alternative embodiment, the flange 36f is adjustable in the manner described with respect to FIG. 5 and the compressed spring 62 biases against the flange 36f, thus locking the flange in place.

Figure 7:
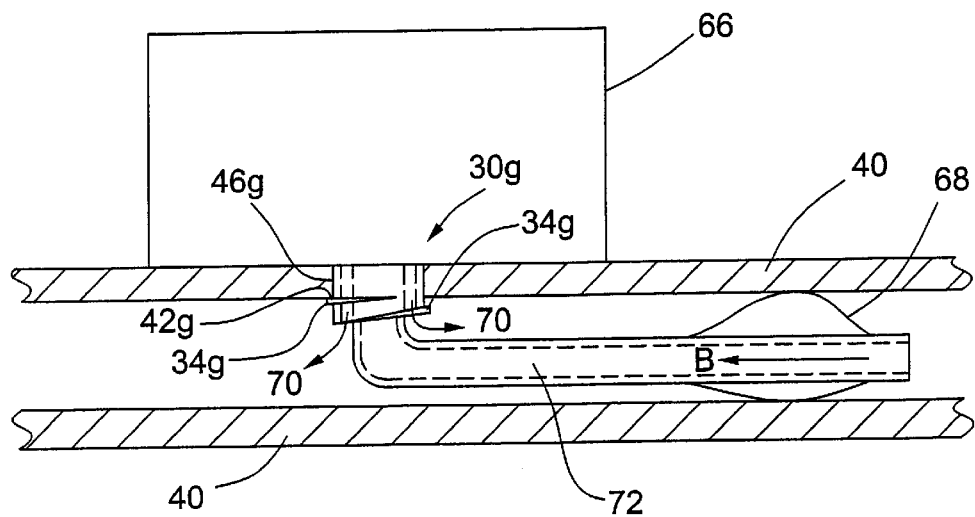
FIG. 7 is a side view of another embodiment of the sealing cannula device connected to an external blood pump.

FIG. 7 shows an embodiment in accordance with the invention in which the sealing cannula device 30g is incorporated into various surgical instruments, including but not limited to a blood pump 66. Before describing the details of the present embodiment, an example of a blood pump will be described along with the advantages of combining the blood pump with the present invention.

A sterile blood pump may be connected to a patient by a coaxial tube which transports the patient's blood to and from the blood pump. The blood pump has an axial blood inlet and a tangential blood outlet or vice versa. An impeller within the fully enclosed and sterile blood pump moves the blood from the inlet to the outlet.

The long lengths of coaxial tubing used to connect the blood pump to the patient increase the priming volume of the blood pump which is the amount of the patient's blood and/or saline which must be drawn into the tubing and the pump to prime the pump before blood begins to be returned to the patient. Long lengths of tubing connecting the pump to the patient also increase the amount of foreign material which comes into contact with the patient's blood, increasing trauma to the patient. It is desirable to minimize the priming volume of the blood pump by placing the blood pump as close as possible to the surgical site and even within the chest cavity. By placing the blood pump close to or within the surgical field, the amount of saline required to prime the bypass circuit is reduced which reduces the likelihood that a transfusion will be required.

Thus, incorporation of the sealing cannula device 30g into a blood pump 66 eliminates the need to utilize an outer cannula as an intermediary connector between the surgical instrument to the sealing cannula device. As shown, the cannula sleeve 46g is connected directly to the blood pump 66 and provides a blood outlet or inlet 70 (shown in FIG. 7 as an outlet) while an inner cannula or conduit 72 formed of a soft, flexible material forming a generally L-shape provides a blood inlet or outlet (shown in FIG. 7 as an inlet). The sealing cannula device 30g may be equipped to support other tools, such as a balloon 68, which is inflated with a fluid such as saline or carbon dioxide gas. The fluid is delivered to the balloon 68 through an auxiliary lumen (not shown) of the inner conduit 72. An inflating device is provided for supplying the bio-compatible fluid. The auxiliary lumen has a distal opening which allows fluid to pass from the auxiliary lumen through a side wall of the inner conduit 72 into the balloon 68. Once inflated, the balloon 68 provides a seal within the blood vessel 40 between the inner conduit 72 and the distal opening of the cannula sleeve 46g.

In a seventh embodiment, shown in FIG. 8, the sealing cannula device 30h has a thread 34h made of a temperature sensitive material such that when the device changes temperature, a free end of the thread 34h moves in a direction of the arrow E. At its initial temperature, the spiraling threads 34h are in the position indicated in hidden lines in FIG. 8 allowing the user to insert and screw the cannula sleeve 46h through a puncture made in a body cavity or vessel wall 40 until the cavity wall or vessel abuts against the flange 36*h*. The vessel or cavity wall 40 is compressed between the flange 36*h* and the flat surface 42*h*, whereby a seal forms which prevents leakages of gasses or bodily fluids through the incision after inserting the cannula sleeve 46*h*. After the cannula sleeve 46*h* is inserted in the body cavity or vessel wall 40 or during insertion, the sealing cannula device 30*h* is exposed to a temperature change due to external heating or cooling or natural heating or cooling. The thread 34*h* flexes in a direction of the arrow E due to the temperature change and forms a substantially continuous ring with the uppermost thread 74*h*. Any tendency for the cannula 30*h* to withdraw from the vessel or body cavity wall 40 as a surgical instrument (not shown) is being inserted or removed through the bore 48*h* will be greatly reduced by the flange 36*h* and substantially continuous ring formed by the deformed threads.

Figure 10:
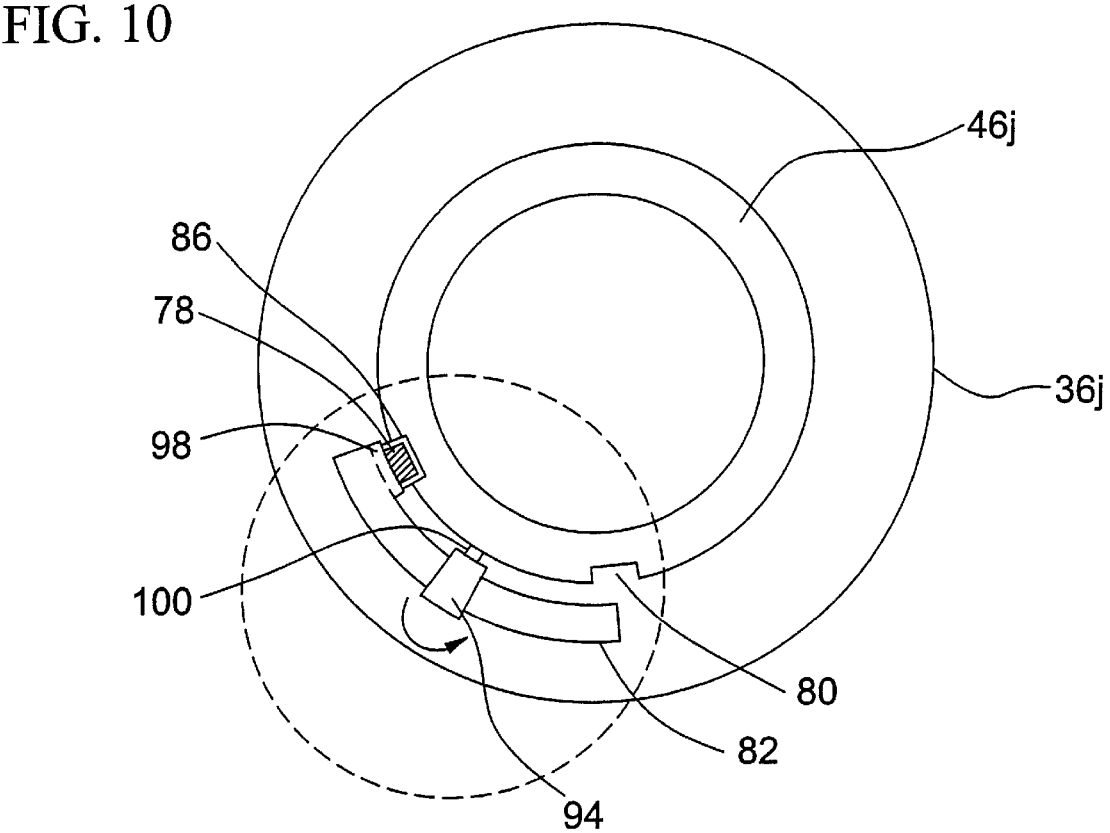
FIG. 10 is a top view of the sealing cannula device of FIG. 9.
Figure 11:
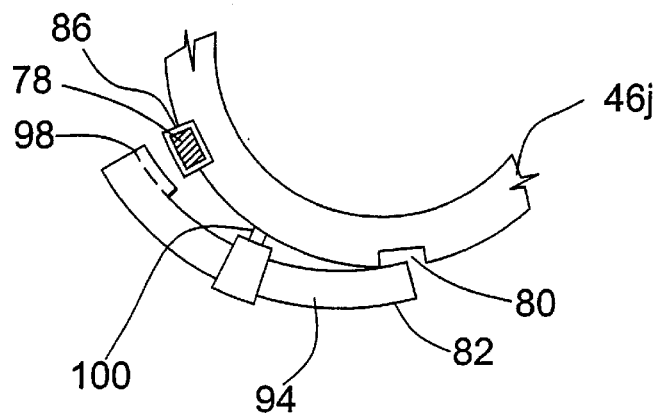
FIG. 11 is an enlarged top view of a portion of the sealing cannula device of FIG. 9 with the locking lever pivotally rotated.

FIGS. 9–11 show another embodiment of the sealing cannula device 30*j* having a pivoting thread 84 on the cannula sleeve 46*j* with a trigger mechanism 78 and a locking lever 82. As shown in FIG. 9, the trigger mechanism 78 is disposed slidably in a direction of the arrow F along the outer surface of the sealing cannula device 30*j*. The trigger mechanism 78 extends transversely through bores 86, 88 in the flange 36*j* and the uppermost thread 74*j*. A distal end 90 of the trigger mechanism 78 has a notch 92 which receives and pivotally rotates the thread 84 about a hinge 76. A proximal end of the trigger mechanism 78 has a plurality of teeth 96 for engaging the locking lever 82 which has mating teeth 98 at one end. The locking lever 82 is mounted to the outside of the cannula sleeve 46*j* by a pivot 94 connected to a stem 100. The cannula sleeve 46*j* has a recess 80 on its outer surface. As shown most clearly in FIG. 11, upon pivotally rotating the locking lever 82 about the pivot 94, the recess 80 accommodates an end of the locking lever and allows the teeth 96 of the trigger mechanism 78 to disengage the mating teeth 98 of the locking lever 82. When the trigger mechanism 78 is disengaged from the locking lever 82, as shown in FIG. 11, the trigger mechanism is slidable along the outer surface of the sealing cannula device 30*j*. The trigger mechanism 78 can move the thread 84 from the open position of FIG. 9 to a closed position in which the threads form a substantially continuous flange to trap the tissue between the flange 36*j* and the threads.

Figure 12:
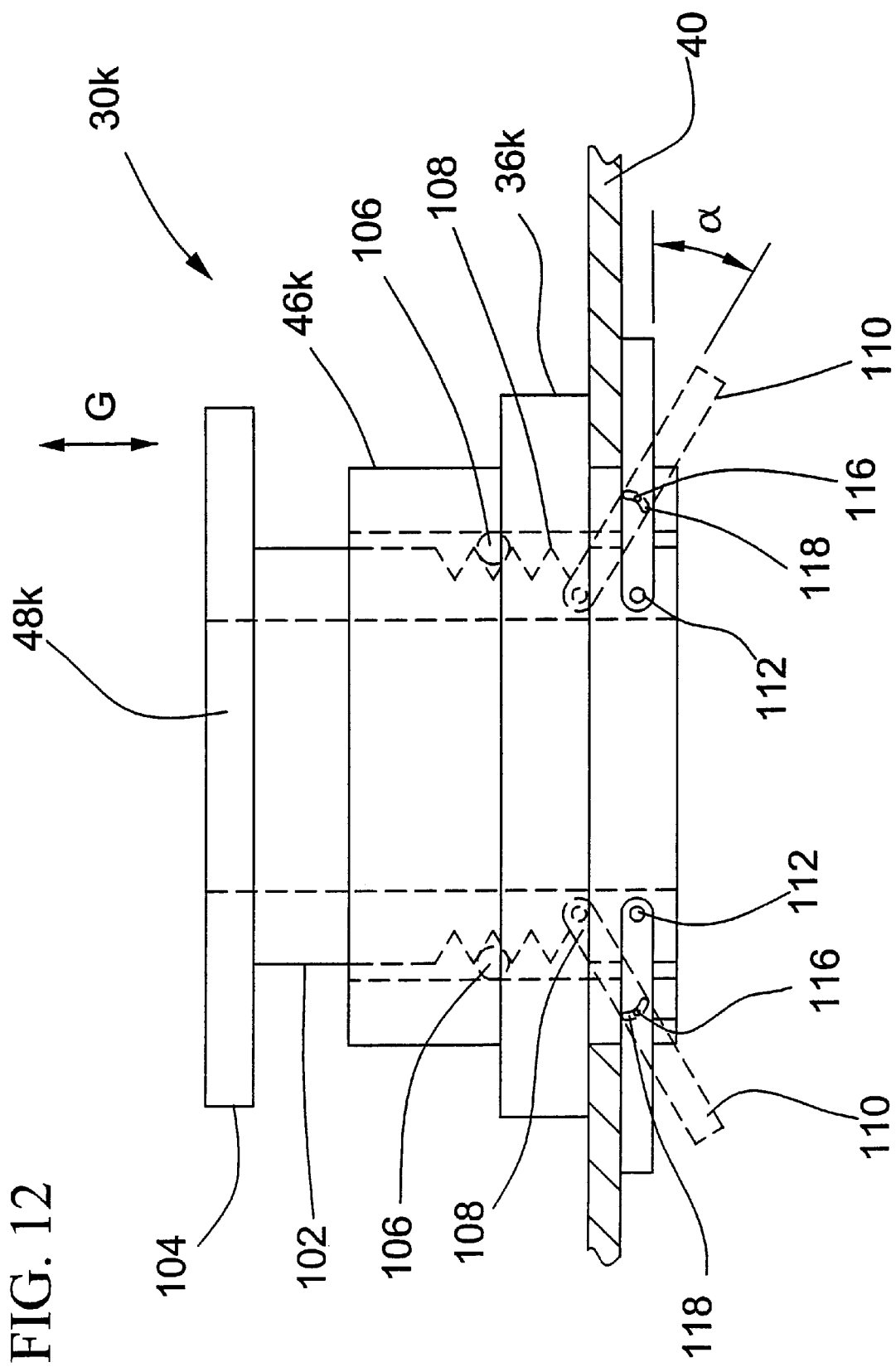
FIG. 12 is a side view of another embodiment of the sealing cannula device having a trigger mechanism which moves hinged members.

In another embodiment of the invention shown in FIG. 12, a trigger mechanism 102 having a handle 104 and a plurality of teeth 108 on its outer surface is mounted within a non-threaded sealing cannula device 30*k* by an engaging member 106. The coaxial trigger mechanism 102 is slidable in a direction of the arrow G along the surface of a central bore 48*k* of the cannula sleeve 46*k*, and the engaging member 106 holds the trigger mechanism in a proper position. Further, the engaging member 106 provides a seal between the trigger mechanism 102 and the cannula sleeve 46*k*, thereby preventing leakage of gasses or bodily fluids from the sealing cannula device 30*k* after insertion in the surgical opening.

The engaging member 106 is fabricated from a soft, flexible material such as rubber or plastic and is secured to an inner surface of the cannula sleeve 46*k*. The trigger mechanism 102 has at least one arm 110, and preferably a plurality of arms, which are hingedly and integrally connected to the trigger mechanism by a flexible joint or hinge 112. Each arm 110 aligns substantially parallel with the axial bore 48*k* for device insertion. Upon moving the trigger mechanism 102 in a direction of the arrow G, the engaging member 106 temporarily deforms to pass over the teeth 108 before resting between two of the teeth, and each arm 110 pivotally rotates about two hinges 112, 116. The hinge 116 includes a hinge pin secured to the cannula sleeve 46*k* and an angled slot 118 in the arm 110 which allows the arm to radially extend at an angle α, such as an angle of 90°. A vessel or cavity wall 40 is compressed between a flange 36*k* and the arms 110 whereby a seal forms which prevents leakage of gasses or bodily fluids through the incision after inserting the sealing cannula device 30*k*.

Figure 13:
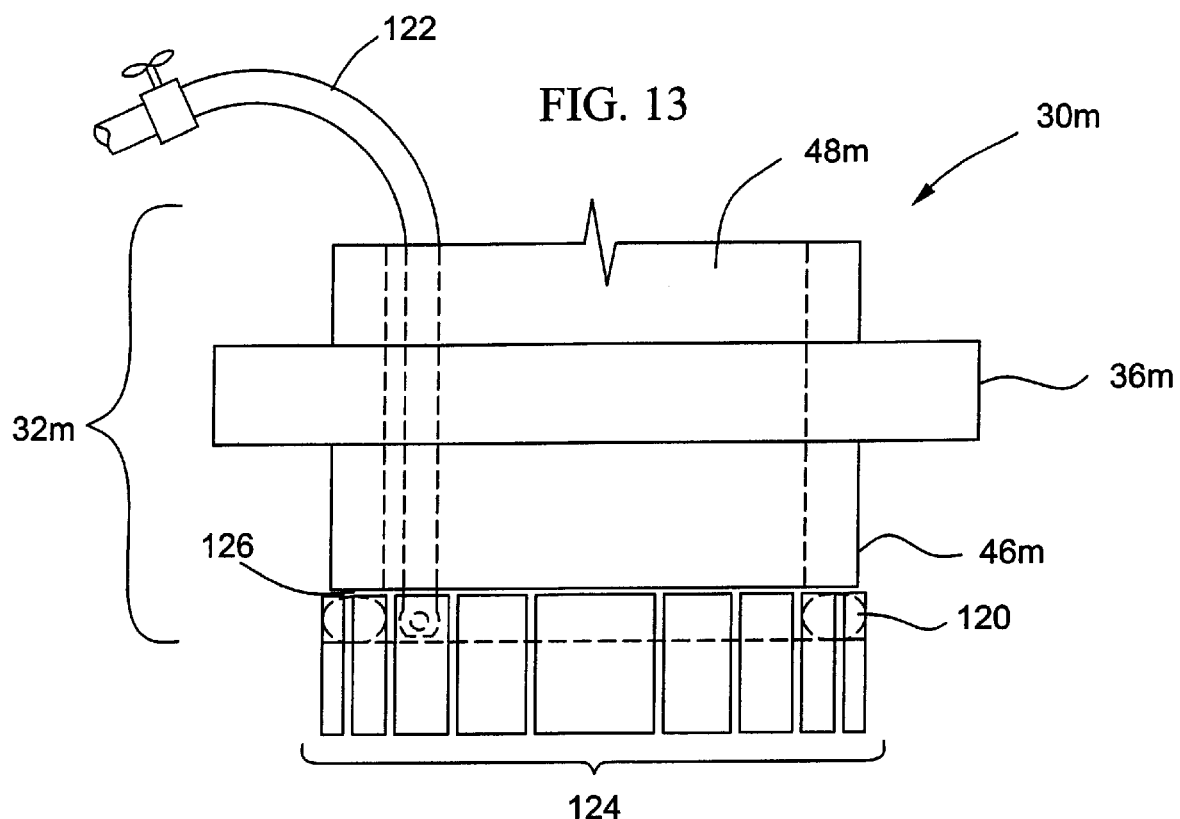
FIG. 13 is a partial side view of another embodiment of the sealing cannula device having an inflatable balloon for moving hinged members.
Figure 14:
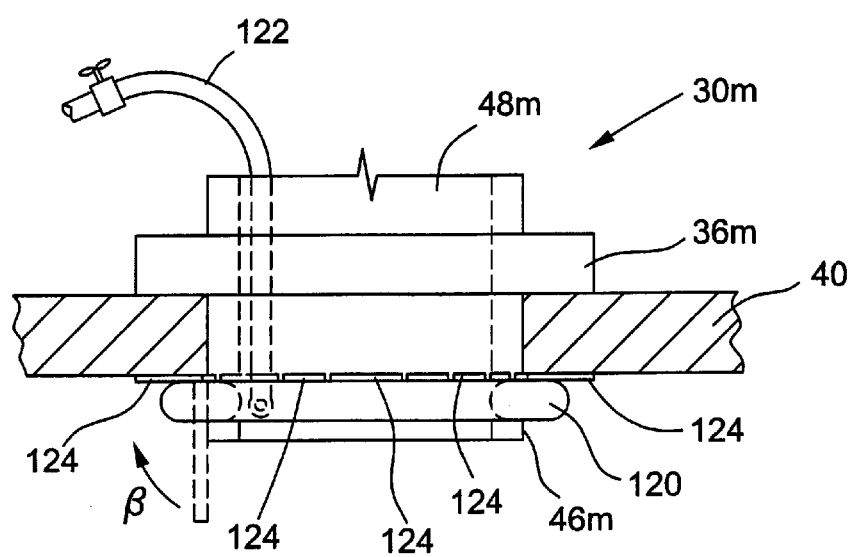
FIG. 14 is a side view of the sealing cannula device of FIG. 13 with an inflated balloon which results in hinged members forming a surface that abuts against a vessel wall.

As shown in FIGS. 13–14, another embodiment of the present invention is a non-threaded sealing cannula device 30*m* having an inflatable balloon 120 which is connected to the cannula sleeve 46*m*. An auxiliary lumen 122 located within the cannula sleeve 46*m* is in fluid communication with the balloon 120 for inflating the balloon. A biocompatible fluid, such as saline or carbon dioxide gas, travels through the lumen 122 and inflates the balloon 120. A plurality of hingedly and integrally connected arms 124 surround the inflatable balloon 120. When the balloon 120 is deflated, each arm 124 aligns substantially parallel with the axial bore 48*m*. As shown most clearly in FIG. 14, the inflated balloon 120 contacts and moves the arms 124 which pivotally rotate about a hinge 126 to a position at which the arms form an angle β with the longitudinal axis of the sealing cannula device 30*m*, such as an angle of 90°. A vessel or cavity wall 40 is then compressed between a flange 36*m* and the arms 124 whereby a seal forms which prevents leakage of gasses or bodily fluids through the incision after inserting the sealing cannula device 30*m*.

Figure 15:
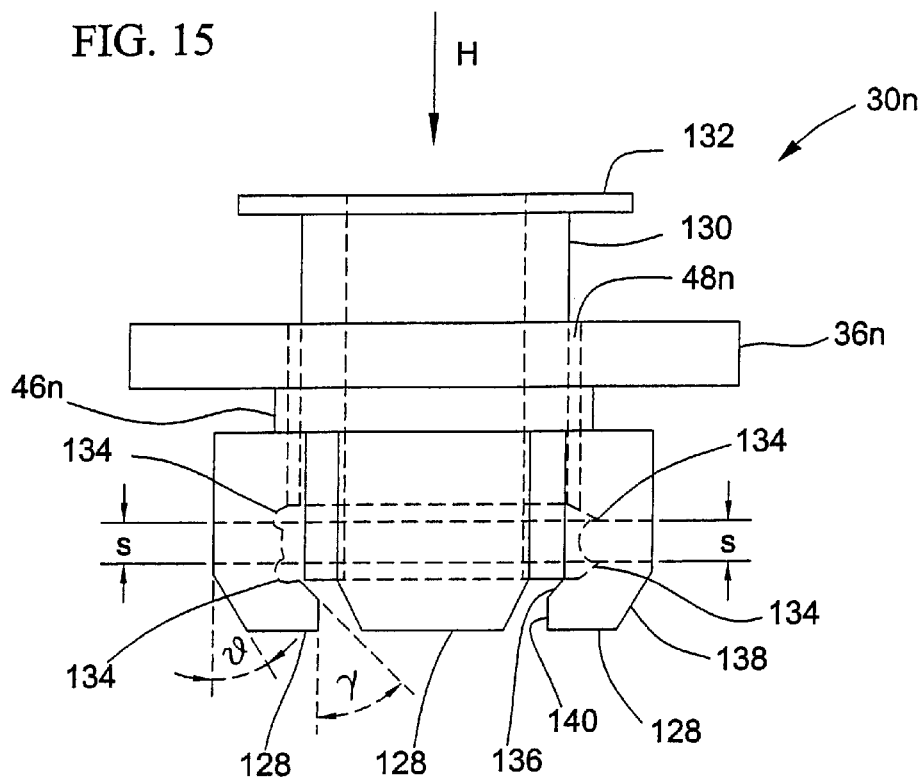
FIG. 15 is side view of another embodiment of the sealing cannula device having a plurality of spring-contact fingers and a trigger mechanism mounted within the cannula.
Figure 16:
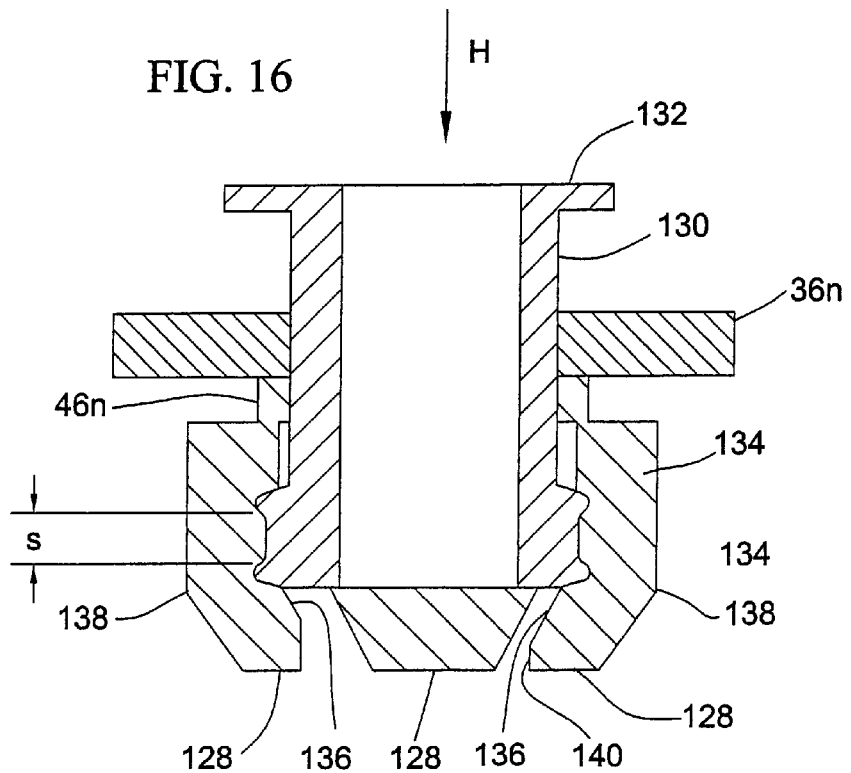
FIG. 16 is a cross-sectional view of the sealing cannula device of FIG. 15.
Figure 17:
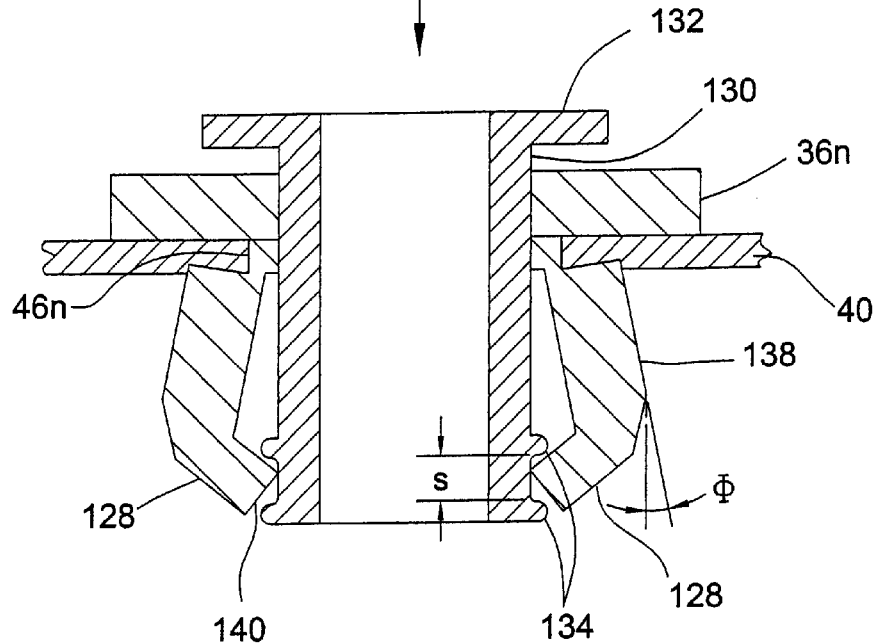
FIG. 17 is a cross-sectional view of the sealing cannula device of FIG. 15 with the trigger mechanism depressed.

As shown in FIGS. 15–17, in another embodiment, a non-threaded sealing cannula device 30*n* has a plurality of spring-contact fingers 128 on the hollow cannula sleeve 46*n* and a coaxial trigger mechanism 130 having a handle 132. Each of the spring-contact fingers 128 has an inside surface 136, an outside surface 138, and a lip 140. The spring-contact fingers 128 are aligned substantially parallel with an axial bore 48*n* in the cannula sleeve 46*n*, as illustrated in FIG. 15, with the inside surfaces 136 facing each other. The inside and outside surfaces 136, 138 taper in a direction toward the axial centerline of the cannula sleeve 46*n* at angles θ and γ, respectively, with respect to a line perpendicular to a plane of the flange 36*n*. The angles θ and γ are less than about 100°. Preferably, the angle γ formed between the inside surfaces 136 and the perpendicular plane of the flange 36*n* is about 30° to about 70°. Preferably, the angle θ formed between the outside surfaces 138 and the perpendicular plane of the flange 36*n* is about 30° to about 70°. Accordingly, an opening between the lips 140 of spring-contact fingers 128 is less than the outer diameter of the trigger mechanism 130 at a distal end.

The trigger mechanism 130 is slidably mounted within the hollow cannula sleeve 46*n*. The trigger mechanism 130 has at least one protrusion 134, and preferably two, at the distal end opposite the handle 132. The handle 132 has been illustrated as a flange 36*n* which extends radially away from the axial bore 48*n*. However, other types of handles may also be used. A space S between the protrusions 134 is chosen to accommodate the lips 140 of the spring-contact fingers 128. Preferably, the space S is in the range of about 0.05 to about 0.2 cm.

As most clearly shown in FIG. 17, when the trigger mechanism 130 moves in a direction of the arrow H, the protrusions 134 contact the spring-contact fingers 128 and move the fingers radially outward by an angle φ. Accordingly, the lips 140 of the spring-contact fingers 128 are accommodated in the space S located between the protrusions 134. The angle φ formed between the outside surface 138 and a perpendicular plane to the flange 36*n* is about 5° to about 45°. A vessel or cavity wall 40 is compressed between a flange 36n and a top surface of the spring-contact fingers 128 whereby a seal forms which prevents leakage of gasses or bodily fluids through the incision after inserting the sealing cannula device 30n. By expanding the fingers 128 in a radially outward direction, the sealing cannula device 30n is more securely mounted within the surgical opening.

In yet another embodiment, the trigger mechanism 130 has no protrusion 134 at the distal end opposite the handle 132. Since the outer diameter of the trigger mechanism 130 is larger than the opening between the lips 140 of the spring-contact fingers 128, when the trigger mechanism moves in a direction of the arrow H, the trigger mechanism contacts the lips. The spring-contact fingers 128 then expand in a radially outward direction, thereby securely mounting the sealing cannula device 30n within the surgical opening.

Figure 18:
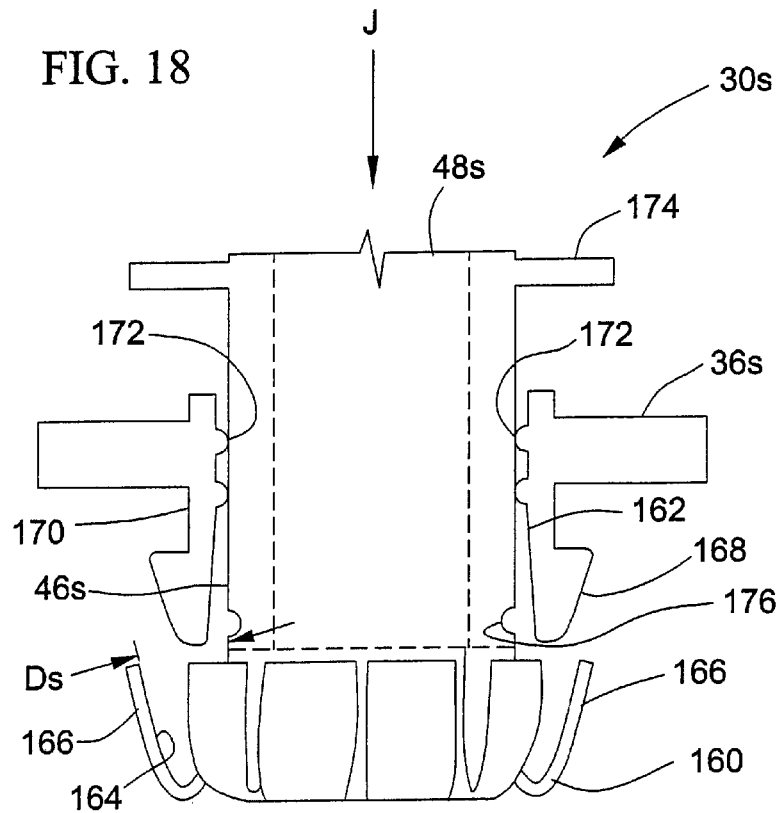
FIG. 18 is a side view of another embodiment of the sealing cannula device having a plurality of flexible spring members and a coaxial trigger mechanism.
Figure 19:
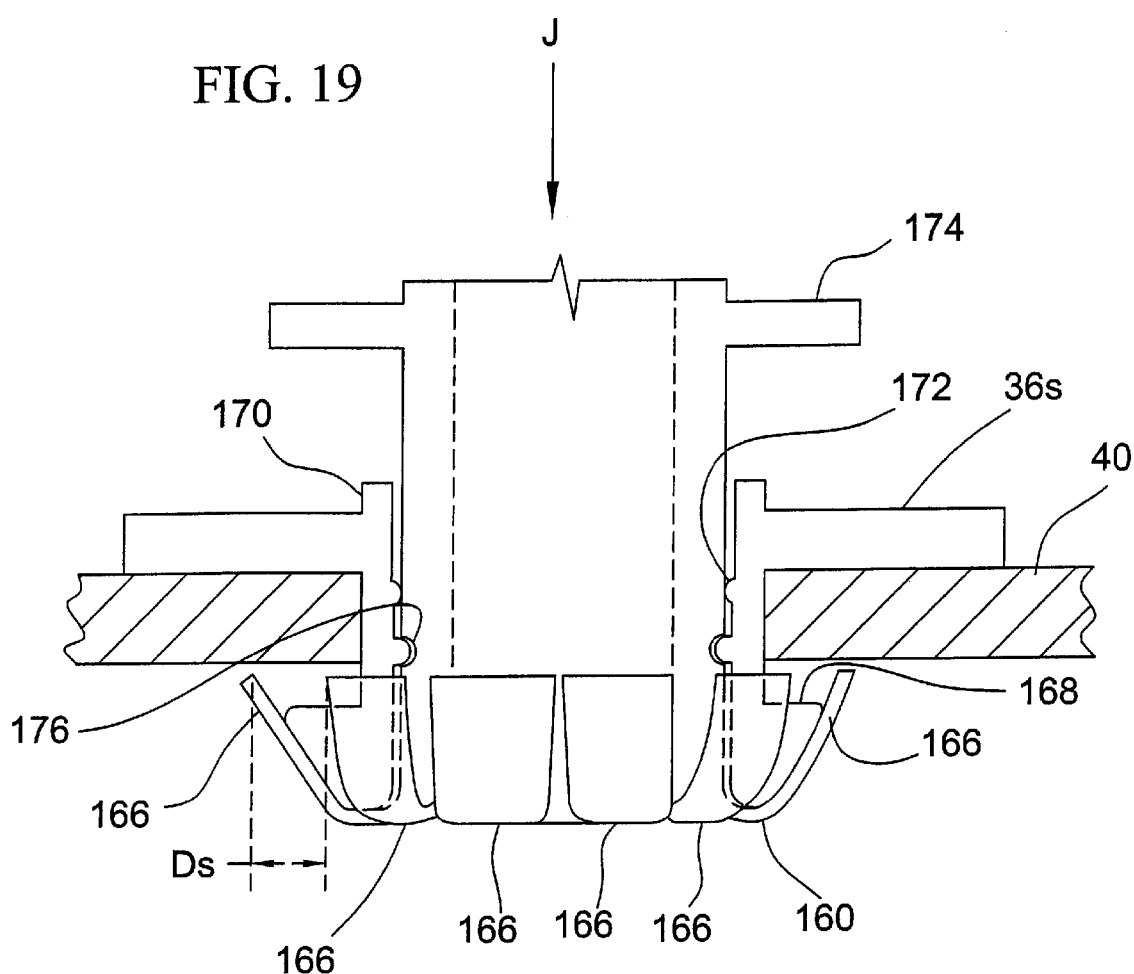
FIG. 19 is a side view of the sealing cannula device of FIG. 18 in an expanded configuration.

As shown in FIGS. 18–19, in a further embodiment, a non-threaded sealing cannula device 30s has a plurality of spring members 166 on the hollow cannula sleeve 46s and an external coaxial trigger mechanism 170. The coaxial trigger mechanism 170 has a wedge-shaped protrusion 168 at the distal end and a flange 36s at a proximal end which extends radially away from the axial bore 48s. The trigger mechanism 170 is slidably mounted outside the cannula sleeve 46s and is movable along the longitudinal axis of said cannula sleeve to expand the spring members 166.

The hollow cannula sleeve 46s includes a handle 174 at the distal end opposite the plurality of spring members 166. The handle 174 extends away from the axial bore 48s, and during use, said handle 174 can contact the trigger mechanism 170, thereby preventing the trigger mechanism 170 from sliding off of the sleeve 46s. The plurality of spring members 166 have outside surfaces 164, and each spring member 166 is bent such that at the free end of each spring member, the outside surfaces face each other at a distance $D_S$. The distance $D_S$ is chosen to be less than the width of the protrusion 168 at its widest point.

In operation, the coaxial trigger mechanism 170 moves in a direction of the arrow J, and the flange 36s contacts the vessel wall 40. As shown most clearly in FIG. 19, the protrusion 168 contacts the plurality of spring members 166 and expands the members in a radially outward direction and increasing the distance $D_S$. The trigger mechanism 170 may be locked in the position shown in FIG. 19 by a locking mechanism. One such locking mechanism includes one or more detents 172 on either the cannula sleeve 46s or the trigger mechanism 170 and corresponding notches 176 on the other part. The at least one detent 172 can mate with the notch 176, and thereby secure the sealing cannula device 30s within the surgical opening and allow the sealing cannula device 30s to provide a seal against said vessel wall 40. When the trigger mechanism 170 includes a variable position locking mechanism, the trigger mechanism can secure the sealing cannula device 30s against the vessel wall 40 at varying degrees of tightness. The locking mechanism may comprise any other suitable means, including but not limited to engaging teeth, clamps, or fasteners.

Figure 20:
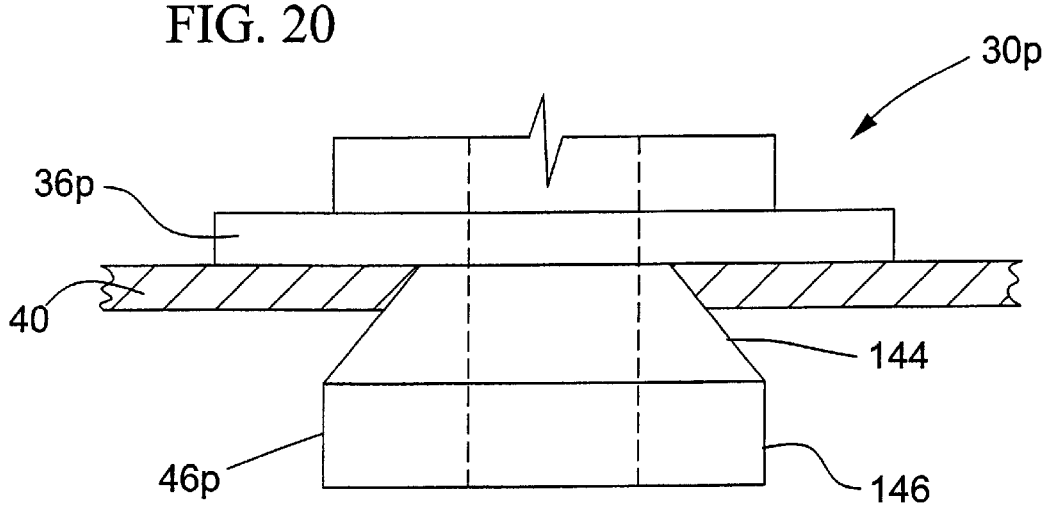
FIG. 20 is a side view of another embodiment of the sealing cannula device having a cannula sleeve with a tapered portion below the flange.

FIG. 20 illustrates another embodiment of the present invention, whereby the non-threaded sealing cannula device 30p includes a hollow cannula sleeve 46p having a flange 36p. The cannula sleeve 46p has a conical cross-sectional portion 144 which tapers from a smallest diameter adjacent the flange to a largest diameter away from the flange 36p. The sealing cannula device 30p also includes a cylindrical portion 146 extending from the largest diameter end of the conical portion 144. Upon inserting the sealing cannula device 30p in the surgical opening, the body cavity or vessel wall 40 will close around the cannula sleeve 46p. The conical cross-sectional configuration will bias the vessel wall 40 against the flange 36p, thereby improving the seal between the tissue and the device 30p.

Figure 21:
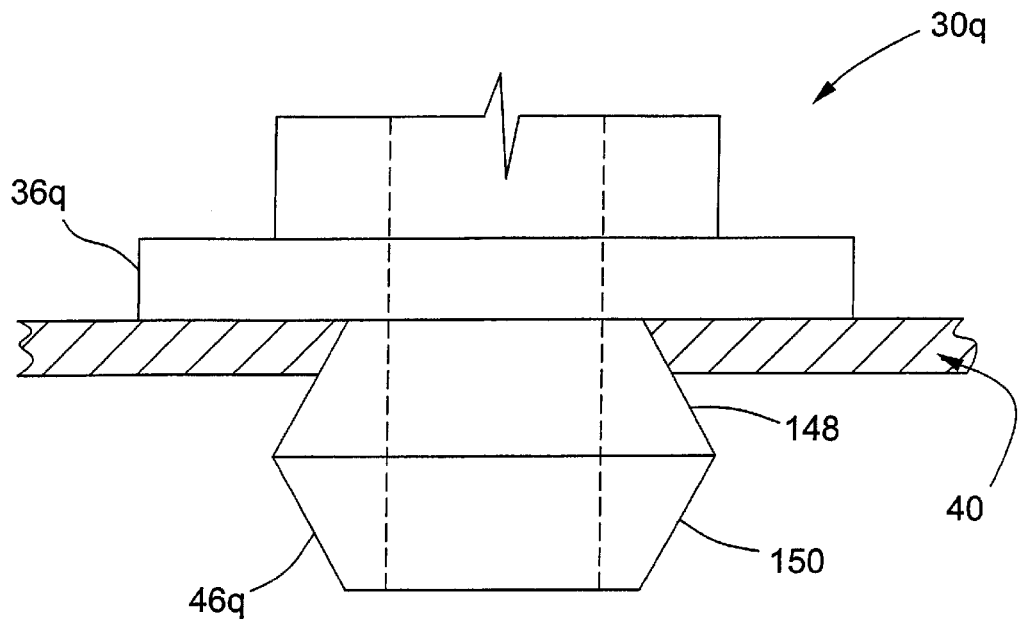
FIG. 21 is a partial side view of another embodiment of the sealing cannula device.

As shown in FIG. 21, in a further embodiment of the present invention, the non-threaded sealing cannula device 30q includes a flange 36q and a hollow cannula sleeve 46q having a first conical cross-sectional portion 148 and a second conical cross-sectional portion 150. The first conical cross-sectional portion 148 tapers from a smallest diameter adjacent the flange 36q to a largest diameter at a distal end away from the flange. A largest diameter of the second conical cross-sectional portion 150 extends from the distal end of the first conical cross-sectional portion 148 and tapers to a smallest diameter away from the flange 36q. The first conical cross-sectional portion 148 will bias the vessel wall 40 against the flange 36q, thereby improving the seal between the tissue and the device 30q. The second conical cross-sectional portion 150 will assist the user when inserting the sealing cannula device 30q in the surgical opening.

Figure 22:
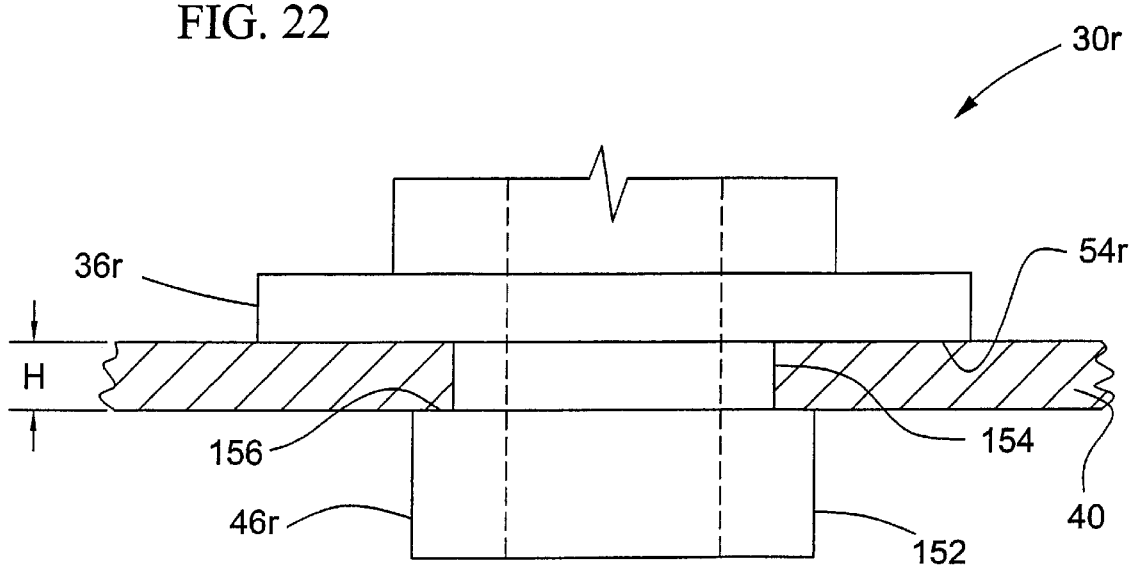
FIG. 22 is a partial side view of another embodiment of the sealing cannula device.

In FIG. 22, the sealing cannula device 30r has a flange 36r and a hollow cannula sleeve 46r having a first cylindrical portion 154 and a second cylindrical portion 152. The height H of the second cylindrical portion 152 is chosen to provide a compression fit between the bottom surface 54r of the flange 36r and the top surface 156 of the first cylindrical portion 154 against the body cavity or vessel wall 40. The outer surface of the cannula sleeve 46r may alternatively be cylindrical (as shown in FIG. 22) or other suitable cross-sectional configuration, including but not limited to square, rectangular, or hexagonal.

In any of the foregoing embodiments, the axial bore 48 may have various configurations, including but not limited to cylindrical or conical. Likewise, in any of the foregoing embodiments, the sealing cannula device can receive a hemostasis valve.

The present invention provides advantages of a single means for securing a cannula in the proper position while providing vascular or body cavity access during surgical or non-surgical procedures. Further, an effective seal is formed between the device and cavity or vessel wall which protects the puncture site from environmental contaminants.

While the invention has been described in detail with reference to the preferred embodiments thereof, it will be apparent to one skilled in the art that various changes and modifications can be made and equivalents employed, without departing from the present invention.

What is claimed is:

1. A sealing cannula for inserting through body tissue and forming a passageway through the body tissue for inserting medical instruments, the sealing cannula comprising:

a hollow cylindrical member having an exterior surface;

a flange extending from said exterior surface and having an upper surface and a lower surface; and a thread on the exterior surface of said cylindrical member which terminates at a thread end spaced a distance from the lower surface of the flange sufficient to accommodate a layer of body tissue, the thread end having a planar surface substantially parallel to the lower surface of said flange such that the planar surface of the thread end and the lower surface of the flange cooperate to compress upon the layer of body tissue when the hollow cylindrical member is threaded into an aperture formed in the layer of body tissue to thereby automatically seal the aperture against leakage along the exterior surface of the cylindrical member.

2. The sealing cannula of claim 1, wherein an angle between the substantially parallel first surface of said flange and the planar surface of said thread is in the range of about 0° to about 15°.

3. The sealing cannula of claim 1, wherein the flange includes a concave surface which faces the body tissue when the hollow cylindrical member has been inserted into the body tissue.

4. The sealing cannula of claim 1, wherein the flange includes a lipped surface which faces the body tissue when the hollow cylindrical member has been inserted into the body tissue.

5. The sealing cannula of claim 1, further comprising a second thread on the exterior surface of said cylindrical member for receiving another cannula or other device.

6. The sealing cannula of claim 1, further comprising means for moving the flange in an axially movable manner.

7. The sealing cannula of claim 6, wherein the means for moving the flange in an axially movable manner comprises a second thread on the exterior surface of said cylindrical member which threadedly receives a threaded inner surface of the flange in an axially movable manner.

8. The sealing cannula of claim 1, further comprising means for biasing the flange against the body tissue.

9. The sealing cannula of claim 1, further comprising a second flange on the exterior surface of said cylindrical member, wherein a spring is positioned between the flange and the second flange, said spring biasing the flange against the body tissue.

10. The sealing cannula of claim 1, wherein the thread is made of temperature sensitive material and moves from a first insertion position to a second sealing position due to a change in temperature, the thread in said second sealing position forms a substantially continuous ring substantially parallel to the first surface of said flange to create a seal with the body tissue.

11. The sealing cannula of claim 1, further comprising a slidable member which engages a positioning lever, whereby said slidable member moves the thread from a first insertion position to a second sealing position, the thread in said second sealing position forms a substantially continuous ring substantially parallel to the first surface of said flange to create a seal with the body tissue.

12. A sealing cannula for inserting through body tissue and forming a passageway through the body tissue for inserting medical instruments, the sealing cannula comprising:

a hollow cylindrical member having an exterior surface;

a flange extending from said exterior surface and having a first surface;

a thread on the exterior surface of said cylindrical member which terminates at a thread end spaced a distance from the first surface of the flange sufficient to accommodate tissue, the thread end having a planar surface substantially parallel to the first surface of said flange to create a seal with the body tissue; and a hemostasis valve such that an inner lumen of said cylindrical member can be at least partially sealed.

13. A sealing cannula coupled with a surgical instrument for inserting through body tissue and forming a passageway through the body tissue thereby eliminating a separate attachment means between the surgical instrument and cannula, the sealing cannula comprising:

a hollow cylindrical member having an exterior surface;

a surgical instrument having a lower surface; and a thread on the exterior surface of said cylindrical member which terminates at a thread end spaced a distance from the lower surface of the surgical instrument sufficient to accommodate a layer of body tissue, said thread end having a substantially planar surface substantially parallel to the lower surface of said surgical instrument such that the planar surface of the thread end and the lower surface of the surgical instrument cooperate to compress upon the layer of body tissue when the hollow cylindrical member is threaded into an aperture formed in the layer of body tissue to thereby automatically seal the aperture against leakage along the exterior surface of the cylindrical member.

14. The sealing cannula of claim 13, wherein the hollow cylindrical member is made of a flexible material.

15. The sealing cannula of claim 13, wherein the surgical instrument is a pump.

* * * * *